United States Patent
Venkatesh et al.

(10) Patent No.: US 8,367,111 B2
(45) Date of Patent: *Feb. 5, 2013

(54) EXTENDED RELEASE DOSAGE FORMS OF PROPRANOLOL HYDROCHLORIDE

(75) Inventors: Gopi M. Venkatesh, Vandalia, OH (US); Krishna S. Vishnupad, Dayton, OH (US); Phillip J. Percel, Troy, OH (US)

(73) Assignee: Aptalis Pharmatech, Inc., Vandalia, OH (US)

( * ) Notice: Subject to any disclaimer, the term of this patent is extended or adjusted under 35 U.S.C. 154(b) by 411 days.

This patent is subject to a terminal disclaimer.

(21) Appl. No.: 10/335,295

(22) Filed: Dec. 31, 2002

(65) Prior Publication Data
US 2004/0126427 A1    Jul. 1, 2004

(51) Int. Cl.
*A61K 9/14* (2006.01)
(52) U.S. Cl. ........................................................ 424/489
(58) Field of Classification Search .................. 424/451
See application file for complete search history.

(56) References Cited

U.S. PATENT DOCUMENTS

| | | | |
|---|---|---|---|
| 3,184,386 A | 5/1965 | Stephenson | |
| 3,558,768 A | 1/1971 | Klippel | |
| 3,885,026 A | 5/1975 | Heinemann et al. | |
| 4,078,051 A | 3/1978 | Pomot et al. | |
| 4,138,475 A | 2/1979 | McAinsh et al. | |
| 4,248,857 A | 2/1981 | DeNeale et al. | |
| 4,292,017 A | 9/1981 | Doepel | |
| 4,305,502 A | 12/1981 | Gregory et al. | |
| 4,369,172 A | 1/1983 | Schor et al. | |
| 4,371,516 A | 2/1983 | Gregory et al. | |
| 4,389,330 A | 6/1983 | Tice et al. | |
| 4,389,393 A | 6/1983 | Schor et al. | |
| 4,542,042 A | 9/1985 | Samejima et al. | |
| 4,556,678 A | 12/1985 | Hsiao | |
| 4,587,118 A | 5/1986 | Hsiao | |
| 4,628,098 A | 12/1986 | Nohara et al. | |
| 4,661,647 A | 4/1987 | Serpelloni et al. | |
| 4,670,459 A | 6/1987 | Sjoerdsma | |
| 4,689,333 A | 8/1987 | Nohara et al. | |
| 4,698,101 A | 10/1987 | Koivurinta | |
| 4,708,867 A | 11/1987 | Hsiao | |
| 4,713,248 A | 12/1987 | Kjornaes et al. | |
| 4,716,041 A | 12/1987 | Kjornaes et al. | |
| 4,728,512 A | 3/1988 | Mehta et al. | |
| 4,743,248 A | 5/1988 | Bartoo et al. | |
| 4,752,470 A * | 6/1988 | Mehta | 424/458 |
| 4,757,090 A | 7/1988 | Salpekar et al. | |
| 4,760,093 A | 7/1988 | Blank et al. | |
| 4,780,318 A | 10/1988 | Appelgren et al. | |
| 4,786,508 A | 11/1988 | Ghebre-Sellassie et al. | |
| 4,800,087 A | 1/1989 | Mehta | |
| 4,803,213 A | 2/1989 | Iida et al. | |
| 4,824,675 A | 4/1989 | Wong et al. | |
| 4,832,880 A | 5/1989 | Staniforth | |
| 4,840,799 A | 6/1989 | Appelgren et al. | |
| 4,851,226 A | 7/1989 | Julian et al. | |
| 4,851,229 A | 7/1989 | Magruder et al. | |
| 4,863,742 A | 9/1989 | Panoz et al. | |
| 4,871,549 A | 10/1989 | Ueda et al. | |
| 4,874,613 A | 10/1989 | Hsiao | |
| 4,886,669 A | 12/1989 | Ventouras | |
| 4,892,741 A | 1/1990 | Ohm et al. | |
| 4,894,240 A | 1/1990 | Geoghegan et al. | |
| 4,898,737 A | 2/1990 | Panoz et al. | |
| 4,915,949 A | 4/1990 | Wong et al. | |
| 4,938,968 A | 7/1990 | Mehta | |
| 4,946,684 A | 8/1990 | Blank et al. | |
| 4,957,745 A | 9/1990 | Jonsson et al. | |
| 4,968,508 A | 11/1990 | Oren et al. | |
| 4,971,805 A | 11/1990 | Kitanishi et al. | |
| 4,983,401 A | 1/1991 | Eichel et al. | |
| 5,006,345 A | 4/1991 | Lang | |
| 5,011,692 A | 4/1991 | Fujioka et al. | |
| 5,013,557 A | 5/1991 | Tai | |
| 5,013,743 A | 5/1991 | Iwahi et al. | |

(Continued)

FOREIGN PATENT DOCUMENTS

| | | |
|---|---|---|
| EP | 0052492 B1 | 2/1984 |
| EP | 0166440 A2 | 1/1986 |

(Continued)

OTHER PUBLICATIONS

Yamahara et al, Effect of release rate on bioavailability of control-release multiple unit dosage forms, 1995, Yakuzaigaku, vol. 55 No. 2, 99-107.*

(Continued)

*Primary Examiner* — Alton Pryor
(74) *Attorney, Agent, or Firm* — Cooley LLP

(57) ABSTRACT

A unit dosage form, such as a capsule or the like for delivering drugs into the body in a sustained release fashion similar to that produced by INDERAL® LA indicated for the treatment of cardiovascular diseases, comprises two populations of propranolol-containing particles (beads, pellets, granules, etc.). Each bead population exhibits a pre-designed rapid release profile (i.e., substantially complete release within 60 minutes) or sustained release profile over a period of 24 hours. Such a cardiovascular drug delivery system is designed by combining immediate release (IR) beads and sustained release (SR) beads. SR beads may be obtained by membrane coating IR beads with a water-insoluble polymer such as ethylcellulose or a mixture of a water insoluble polymer and a water-soluble polymer such as hydroxypropylcellulose at a ratio of from about 65/35 to 95/5.

25 Claims, 5 Drawing Sheets

U.S. PATENT DOCUMENTS

| | | |
|---|---|---|
| 5,017,122 A | 5/1991 | Staniforth |
| 5,017,381 A | 5/1991 | Maruyama et al. |
| 5,026,559 A | 6/1991 | Eichel et al. |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bucheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A | 11/1993 | Chen |
| 5,275,827 A | 1/1994 | Spinelli et al. |
| 5,376,384 A | 12/1994 | Eichel et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A * | 12/1995 | Eichel et al. .................. 424/480 |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chaveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A | 10/2000 | Grimmett et al. |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1 | 4/2002 | Khankari et al. |
| 6,368,625 B1 | 4/2002 | Siebert et al. |
| 6,368,628 B1 | 4/2002 | Seth |
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Chittamuru et al. |
| 6,432,534 B1 | 8/2002 | Hayakawa et al. |
| 6,465,009 B1 | 10/2002 | Liu et al. |
| 6,465,010 B1 | 10/2002 | Lagoviyer et al. |
| 6,495,160 B2 | 12/2002 | Esposito et al. |
| 6,500,454 B1 * | 12/2002 | Percel et al. .................. 424/451 |
| 6,509,036 B2 | 1/2003 | Pather et al. |
| 6,531,152 B1 | 3/2003 | Lerner et al. |
| 6,551,617 B1 | 4/2003 | Corbo et al. |
| 6,579,535 B2 | 6/2003 | Valentine et al. |
| 6,596,311 B1 | 7/2003 | Dobetti |
| 6,602,521 B1 * | 8/2003 | Ting et al. .................. 424/471 |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 | 12/2003 | Percel et al. |
| 6,663,893 B2 | 12/2003 | Corbo et al. |
| 6,740,341 B1 | 5/2004 | Holt et al. |
| 6,897,205 B2 | 5/2005 | Beckert et al. |
| 7,048,945 B2 | 5/2006 | Percel et al. |
| 2001/0007680 A1 | 7/2001 | Kolter et al. |
| 2001/0014340 A1 | 8/2001 | Ohta et al. |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1 | 12/2002 | Cade et al. |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 * | 8/2003 | Percel et al. .................. 424/473 |
| 2003/0161888 A1 | 8/2003 | Fernandez et al. |
| 2003/0215500 A1 | 11/2003 | Ohta et al. |
| 2004/0047906 A1 | 3/2004 | Percel et al. |
| 2004/0121010 A1 | 6/2004 | Hirsh et al. |
| 2004/0122106 A1 | 6/2004 | Ohta et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Bruschi et al. |
| 2006/0057199 A1 | 3/2006 | Venkatesh et al. |
| 2006/0078614 A1 | 4/2006 | Venkatesh et al. |
| 2006/0105038 A1 | 5/2006 | Lai et al. |
| 2006/0105039 A1 | 5/2006 | Lai et al. |

| | | | |
|---|---|---|---|
| 2006/0246134 A1 | 11/2006 | Venkatesh | |
| 2006/0269607 A1 | 11/2006 | Percel et al. | |
| 2009/0263480 A1 | 10/2009 | Lai et al. | |

FOREIGN PATENT DOCUMENTS

| | | |
|---|---|---|
| EP | 0239361 | 9/1987 |
| EP | 0349103 A1 | 1/1990 |
| EP | 0357369 A2 | 3/1990 |
| EP | 0391518 | 10/1990 |
| EP | 0431877 A1 | 6/1991 |
| EP | 0516345 A1 | 12/1992 |
| EP | 0538034 A1 | 4/1993 |
| EP | 0553777 A2 | 8/1993 |
| EP | 0650826 A1 | 5/1995 |
| EP | 0721777 A2 | 7/1996 |
| EP | 0815931 A1 | 1/1998 |
| EP | 0294493 A1 | 12/1998 |
| EP | 0914818 A1 | 5/1999 |
| EP | 0914823 A1 | 5/1999 |
| EP | 1010423 A2 | 6/2000 |
| EP | 0582396 BI | 1/2001 |
| EP | 1070497 A1 | 1/2001 |
| EP | 1072257 A1 | 1/2001 |
| EP | 1157690 A1 | 11/2001 |
| EP | 1156686 B1 | 3/2003 |
| EP | 1366759 A1 | 12/2003 |
| EP | 0914823 B1 | 12/2004 |
| EP | 2319498 A1 | 5/2011 |
| FR | 2679451 A1 | 1/1993 |
| FR | 2766089 A1 | 1/1999 |
| FR | 2778848 A1 | 11/1999 |
| GB | 2053787 A | 2/1981 |
| GB | 8824392.8 | 9/1989 |
| GB | 2224207 A | 5/1990 |
| JP | 41-11273 B | 6/1966 |
| JP | 49-69819 | 7/1974 |
| JP | 55-129224 A | 10/1980 |
| JP | 56-014098 A | 10/1981 |
| JP | 61-143316 A | 7/1986 |
| JP | 62-50445 B2 | 10/1987 |
| JP | 62-242616 A | 10/1987 |
| JP | 62-246513 A | 10/1987 |
| JP | 62-252723 A | 11/1987 |
| JP | 63-162619 A | 7/1988 |
| JP | 63-270624 A | 11/1988 |
| JP | 1-503385 A | 11/1989 |
| JP | 1-313420 A | 12/1989 |
| JP | 2-500747 A | 3/1990 |
| JP | 2-164824 A | 6/1990 |
| JP | 2-172918 A | 7/1990 |
| JP | 2-289512 A | 11/1990 |
| JP | 3-240724 A | 10/1991 |
| JP | 5-271054 A | 10/1993 |
| JP | 5-310558 A | 11/1993 |
| JP | 6-53658 B2 | 7/1994 |
| JP | 6-321790 A | 11/1994 |
| JP | 7-69889 A | 3/1995 |
| JP | 7-124231 A | 5/1995 |
| JP | 8-503482 A | 4/1996 |
| JP | 8-175978 A | 7/1996 |
| NZ | 550608 A | 11/2005 |
| NZ | 554346 A | 5/2006 |
| WO | WO 88/08703 A1 | 11/1988 |
| WO | WO 88/08704 A2 | 11/1988 |
| WO | WO 92/10173 A1 | 6/1992 |
| WO | WO 93/00097 A1 | 1/1993 |
| WO | WO 93/12769 A1 | 7/1993 |
| WO | WO 93/13758 A1 | 7/1993 |
| WO | WO 93/15724 A1 | 8/1993 |
| WO | WO 94/08576 A1 | 4/1994 |
| WO | WO 94/12180 A1 | 6/1994 |
| WO | WO 97/41878 A1 | 11/1997 |
| WO | WO 97/47287 A1 | 12/1997 |
| WO | WO 99/04763 A1 | 2/1999 |
| WO | WO 00/25752 A1 | 5/2000 |
| WO | WO 00/33821 A1 | 6/2000 |
| WO | WO 00/42998 A1 | 7/2000 |
| WO | WO 00/51568 A1 | 9/2000 |
| WO | WO 00/59486 A2 | 10/2000 |
| WO | WO 01/13898 A2 | 3/2001 |
| WO | WO 01/72285 A1 | 10/2001 |
| WO | WO 01/80829 A2 | 11/2001 |
| WO | WO 02/13794 A1 | 2/2002 |
| WO | WO 02/43704 A1 | 6/2002 |
| WO | WO 02/057475 A1 | 7/2002 |
| WO | WO 02/085336 A1 | 10/2002 |
| WO | WO 03/013492 A1 | 2/2003 |
| WO | WO 03/039520 A1 | 3/2003 |
| WO | WO 03/026613 A1 | 4/2003 |
| WO | WO 03/041683 A2 | 5/2003 |
| WO | WO 03/047552 A2 | 6/2003 |
| WO | WO 2004/009058 A1 | 1/2004 |
| WO | WO 2004/022037 A1 | 3/2004 |
| WO | WO 2004/087111 A1 | 10/2004 |
| WO | WO 2005/097064 A2 | 10/2005 |
| WO | WO 2005/105049 A2 | 11/2005 |

OTHER PUBLICATIONS

Ishino, R et al., "Design and Preparation of Pulsatile Release Tablet as a New Oral Drug Delivery System," Chem. Pharm. Bull., vol. 40, No. 11, pp. 3036-3041 (Nov. 1992).

Anwar, Y. et al., "Chronotherapeutics for Cardiovascular Disease," Drugs, May 1998.

"Low Substituted Hydroxypropylcellulose," Official Monographs for Part II, 2001, NRF, JP XIV, pp. 942-943.

Albrecht, "International Search Report," 6 pages, from International Patent Appl. No. PCT/US02/31535, European Patent Office (Feb. 3, 2003).

Bauer et al., Pharmarzeutische Technologie, 5$^{th}$ Edition, 1997, Govi Verlag Frankfurt, pp. 164-166.

Berigan, "Atomoxetine Used Adjunctively With Selective Serotonin Reuptake Inhibitors to Treat Depression," Prim. Care. Companion J. Clin. Psychiatry 6(2):93-94 (2004).

Bodmeier et al., "Theophylline Tablets Coated with Aqueous Latexes Containing Dispersed Pore Formers," J. Pharm. Sci. 79(10):925-928 (1990).

Database WPI, Section Ch, Week 198748, Derwent Publications, Ltd., London, GB; Class A96; AN 1987-338131, XP002156870.

Fell, Letter to the Editor, J. Pharm. Pharmacol. 1968, vol. 20, pp. 657-658.

FMC Corporation Product Specification for Avicel PH, 2005.

Foreign non-patent publication from Japanese textbook, 1989, Hirokawa Publishing Co.

Foreign non-patent publication Sysmex No. FP30SCJ001.

Fubara, "International Preliminary Examination Report," 3 pages, from International Patent Appl. No. PCT/US02/31535, European Patent Office (Jun. 19, 2003).

Gordon et al., "Effect of the Mode of Super Disintegrant Incorproration on Dissolution in Wet Granulated Tables," J. Pharm. Sci. 82:220-226 (1993).

Gorman et al., An Evaluation of Croscarmellose as a Tablet Disintegrant in Direct Compression Systems, Drug. Dev. Ind. Pharm. 1982; vol. 8, pp. 397-410.

Handbook (Binran) of Granule, vol. 1, Ohmsha Ltd., p. 434 & 438 (May 3, 1975).

Kaneto et al., 2000, Latest Pharmacy, Hirokawa Publishing Co., 1 Edition.

Kawashima, "Low-Substituted Hydroxypropylcellulose as a Sustained-Drug Release Matrix Base or Disintegrant Depending on Its Particle Size and Loading in Formulation," Pharm. Res. 1993, vol. 10(3), pp. 351-355.

Kornblum, "A New Tablet Disintegrating Agent," J. Pharm. Sci., Jan. 1973, vol. 62(1), pp. 43-49.

Kratochvil et al., "Atomoxetine: a selective noradrenaline reuptake inhibitor for the treatment of attention-deficit/hyperactivity disorder," Exp. Opin. Pharmacother. 4(7):1165-1174 (2003).

McKenna et al., "Effect of particle size on the compaction mechanism and tensile strength of tablets," J. Pharm. Pharmacol. Jun. 1982, vol. 34(6), pp. 347-351.

McKetta et al., "Table of Contents," Encyclopedia of Chemical Processing and Design (1989).

McKetta et al., Encyclopedia of Chemical Processing and Design, "Organic Phase Separation Conservation," p. 167 (1989).

Mitsuo et al., Pharmaceutics Manual, 1989, Pharmaceutics Manual, Nanzando Co. Ltd.

Nwokole et al., "Tolerance during 29 days of conventional dosing with cimetidine, mizatidine, famotidine or ranitidine," Aliment. Pharmacol. Ther. 4(Suppl. I):29-45 (1990) Abstract only.

Oh, "International Preliminary Report on Patentability," 5 pages, from International Appl. No. PCT/US2005/037084, United States Patent and Trademark Office, Alexandria, Virginia, USA (mailed Aug. 24, 2007).

Ohira et al., "Effects of Various Histamine $H_2$-Receptor Antagonists on Gastrointestinal Motility and Gastric Emptying," J. Smooth Muscle Res. 29:131-142 (1993).

Pharmaceutical Excipients. London: Pharmaceutical Press. Electronic Version, 2006, Mannitol.

Pharmaceutical Excipients. London: Pharmaceutical Press. Electronic Version, 2006, Lactose Monohydrate.

Pharmaceutical Excipients. London: Pharmaceutical Press. Electronic Version, 2006, Croscarmellose sodium.

Rankin, "International Search Report," 6 pages, PCT International Application No. PCT/US02/39238, European Patent Office (May 8, 2003).

Rudnic et al., "Some Effects of Relatively Low Levels of Eight Tablet Disintegrants on a Direct Compression System," Drug. Dev. Ind. Pharm. 1981, vol. 7(3), pp. 347-358.

Rudnic et al., "Studies of the Utility of Cross Linked Polyvinlpolypyrrolidine as a Tablet Disintegrant," Drug Development and Industrial Pharmacy, 1980, vol. 6, No. 3, pp. 291-309.

Sato et al., "Anticonvulsant effects of tigabine, a new antiepileptic drug: the profile of action in the rat kindling model of epilepsy," Epilepsia 37(Supp. 3):110-111 (1996).

Schifferer, "International Search Report," 4 pages, from International Appl. No. PCT/US2005/037084, European Patent Office, Rijswijk, The Netherlands (mailed Jun. 1, 2006).

Schifferer, "Written Opinion of the International Search Authority," 6 pages, from International Appl. No. PCT/US2005/037084, European Patent Office, Munich, Germany (mailed Jun. 1, 2006).

Shangraw et al., "A new era of tablet disintegrants," Pharm. Technol. 1980, vol. 4(10), pp. 49-57.

Tirkkonen and Paronen, "Enhancement of drug release from ethylcellulose microcapsules using solid sodium chloride in the wall," Int. J. Pharmaceutics 88;39-51 (1992).

Trottier and Wood, 2005, "Particle Size Measurement," Kirk-Othmer Encyclopedia of Chemical Technology (Extract of 1. Introduction; 2. Data Representation; 4. Measurement Methods; 8. Selection of Equipment).

Ueki et al., "Nizatidine Comparably Enhances Postprandial Gastric Motility to Existing Gastroprokinetics in Dogs," Jpn. Pharmacol. Ther. 28(11):925-930 (2000).

Uhl, "International Search Report," 5 pages, International Patent Appl. No. PCT/US2006/016538, European Patent Office (Feb. 27, 2007).

Uhl, "Written Opinion of the International Searching Authority," 6 pages, International Patent Appl. No. PCT/US2006/016538, European Patent Office (Feb. 27, 2007).

van Kamp et al., "Improvement by super disintegrants of the properties of tablets containing lactose, prepared by wet granulation," Pharmaceutisch Weekblad Scientific Edition; 1983, vol. 5, pp. 165-171.

Villa, "International Search Report," 4 pages, from International Appl. No. PCT/US2005/038328, European Patent Office, Rijswijk, The Netherlands (mailed Sep. 15, 2006).

Villa, "Written Opinion of the International Search Authority," 5 pages, from International Appl. No. PCT/US2005/038328, European Patent Office, Munich, Germany (mailed Sep. 15, 2006).

Vromans et al., "Studies on tableting properties of lactose," Pharmaceutisch Weekblad Scientific Edition; 1985, vol. 7, pp. 186-193.

Yamamoto et al., "The Effects of Nizatidine on the Function of Esophageal Motility in Patients with Gastroesophageal Reflux Disease (GERD)," Jpn. Pharmacol. Ther. 28(5):419-424 (2000).

Young, "International Preliminary Examination Report" 6 pages, PCT International Application No. PCT/US02/39238, United States Patent and Trademark Office (Apr. 27, 2005).

Young, "Written Opinion," 5 pages, PCT International Application No. PCT/US02/39238, United States Patent and Trademark Office (Jan. 13, 2005).

Zheng et al., "Influence of Eudragit® NE 30 D Blended with Eudragit® L 30 D-55 on the Release of Phenylpropanolamine Hydrochloride from Coated Pellets," Drug Development and Industrial Pharmacy 29(3):357-366 (2003).

Zimmer, "European Search Report," 3 pages, European patent appl. No. 01103129.1, European Patent Office (Jun. 9, 2001).

Zimmer, "International Search Report," 4 pages, PCT International Application No. PCT/US01/04012, European Patent Office (Jun. 19, 2001).

* cited by examiner

EXTENDED RELEASE DOSAGE FORMS OF PROPRANOLOL HYDROCHLORIDE

TECHNICAL FIELD

This invention relates to extended release dosage forms of propranolol hydrochloride suitable for oral administration for the treatment of cardiovascular diseases, exhibiting in vitro and in vivo release profiles matching that of INDERAL® LA (an extended release propranolol hydrochloride dosage form), and more particularly to extended release propranolol HCl capsules, 60, 80, 120, and 160 mg, comprising immediate release (IR) beads releasing the drug within 60 minutes and sustained release (SR) beads releasing the drug over 24 hours when dissolution tested by the United States Pharmacopoeia dissolution test method for propranolol hydrochloride extended release capsules.

BACKGROUND OF THE INVENTION

Propranolol hydrochloride-containing non-pareil seeds (sugar spheres) require a coating of water insoluble ethylcellulose of less than 2% by weight to mimic the drug release profile of INDERAL® LA when applied from a 98/02 acetone/purified water solution. Due to extremely low spray time, a significant batch to batch variability in drug release profile can occur. There was thus a desire to minimize batch to batch variability in drug release profile. Batch to batch variability may be improved by incorporating a water soluble film forming agent in the ethylcellulose membrane such that a significantly higher coating level, less susceptible to batch to batch variation, would be desired to provide a drug release profile mimicking that of INDERAL® LA.

U.S. Pat. No. 4,138,475 to McAinsh et al. discloses controlled release oral formulation comprising coated spheroids of propranolol or a pharmaceutically acceptable salt thereof, each spheroid coated with a mixture of 80 to 100% by weight of ethylcellulose, preferably having a viscosity of 50 cps at 20° C., 20 to 0% by weight of hydroxypropyl methylcellulose and optionally up to 20% plasticizer based on the total weight of the membrane. These spheroids prior to membrane coating comprise 40 to 65% by weight propranolol or a pharmaceutically acceptable salt thereof and 35 to 60% by weight of microcrystalline cellulose and are prepared by extrusion and spheronization. The ratio of ethylcellulose to hydroxypropylcellulose and coating thickness depend upon the desired controlled release characteristics.

U.S. Pat. No. 4,587,118 issued to Hsiao discloses a controlled release theophylline oral formulation comprising coated micropellets; each pellet is designed to release theophylline at an approximately constant rate. The pellet comprises a drug containing core, which is then coated with a mixture of about 90-70% by weight of ethylcellulose and about 10-30% by weight of hydroxypropyl cellulose. The ratio of ethylcellulose to hydroxypropylcellulose and coating thickness depend upon the desired control release characteristics.

U.S. Pat. No. 4,752,470 issued to Mehta teaches the art of making a controlled release indomethacin formulation comprising coated pellets of indomethacin; each pellet is designed to release indomethacin in both immediate and sustained release form. The pellet comprises a drug-containing core, which is then coated with a mixture of plasticized ethylcellulose and hydroxypropyl cellulose or hydroxypropyl methylcellulose. The loaded pellets are preferably composed of 5-30% by weight of indomethacin and coated with 0.5-10% by weight of ethylcellulose and hydroxypropylcellulose or hydroxypropyl methylcellulose, the ratio of ethylcellulose to hydroxypropylcellulose/hydroxypropyl methylcellulose depending upon the desired control release characteristics.

U.S. Pat. No. 4,957,745 issued to Jonsson et al. describes the art of making a controlled release formulation of a salt of metoprolol comprising a multitude of metoprolol cores prepared by layering the drug onto inert silicon dioxide beads, wherein the core is coated with a metoprolol permeable membrane of essentially ethylcellulose or a mixture of hydroxypropyl methylcellulose and ethylcellulose, the ratio of ethylcellulose to hydroxypropyl methylcellulose depending upon the desired control release characteristics.

U.S. Pat. No. 5,133,974 issued to Paradissis et al. discloses a controlled release formulation comprising a mixture of approximately 0-50% immediate release particles containing a drug, an inert substrate, a binder coated with talc, and up to 100% of extended release particles comprising the immediate release particles coated with a dissolution modifying system containing plasticizers and a film forming agent. Optionally, a drug is included in the coating. Film forming agents include ethylcellulose, hydroxypropyl cellulose, hydroxypropyl methylcellulose and mixtures thereof.

U.S. Pat. No. 5,472,708 issued to Chen discloses the art of making a tablet which rapidly disintegrates in the aqueous environment of use, comprising a plurality of pellets embedded in the tablet comprising drug containing cores and a swelling agent having a dissolution rate controlling polymer membrane of a mixture of water-insoluble ethylcellulose and a water soluble film forming polymer, and a permeability reducing agent. The water-soluble polymer is selected from a group containing cellulose acetate phthalate, hydroxypropyl methylcellulose, and polyvinylpyrrolidone, the polymer exhibiting greater solubility at alkaline pH's being preferred. The swelling agent has the property of increasing in volume on exposure to the aqueous environment of use, thus causing rapid release of the drug following bursting of the bead.

Propranolol [1-(isopropyl amino)-3-(1-naphthyloxy)-2-propanoyl] is a beta-adrenergic blocking agent and as such is a competitive inhibitor of the effects of catecholamines at beta-adrenergic receptor sites. The principal effect of propranolol is to reduce cardiac activity by diminishing or preventing beta-adrenergic stimulation. By reducing the rate and force of contraction of the heart, and decreasing the rate of conduction of impulses through the conducting system, the response of the heart to stress and exercise is reduced. These properties are used in the treatment of angina in an effort to reduce the oxygen consumption and increase the exercise tolerance of the heart. Propranolol is also used in the treatment of cardiac arrhythmias to block adrenergic stimulation of cardiac pacemaker potentials. Propranolol is also beneficial in the long-term treatment of hypertension. Other uses of propranolol are in the treatment of migraine and anxiety.

Propranolol is normally administered as propranolol hydrochloride tablets or as long acting INDERAL® LA.

SUMMARY OF THE INVENTION

The present invention provides a sustained release multiparticulate dosage form comprising a two-bead population of propranolol hydrochloride—one IR (immediate release) bead and the other SR (sustained release) bead. Alternatively, the dosage form may comprise only SR beads. The IR bead population, comprising in one embodiment an inert core coated with one or more layers of propranolol HCl and a binder, rapidly releases the active upon oral administration while the SR bead population comprises an IR bead population having a sustained release coating of a water insoluble polymer (e.g., ethylcellulose) or a combination of a water insoluble polymer and a water soluble polymer, such as hydroxypropylcellulose (e.g., HPC, Klucel LF) or hydroxypropyl methylcellulose (e.g., HPMC, Methocel E5). The weight ratio of water insoluble polymer to water soluble polymer may vary from 100:0 to 65:35. The weight of the SR coating may vary from approximately 1 to 10%, preferably from about 1.5 to 4.0% based on the total weight of the coated beads, and most preferably the SR coating level is approximately 1.8 to 4.4 weight % based on the weight of the SR beads.

In accordance with one embodiment of the present invention unit dosage forms of extended release propranolol hydrochloride are provided that will release the drug into an aqueous environment in a fashion mimicking that of INDERAL® LA when tested under in vitro or in vivo conditions. It is an embodiment of the present invention to provide unit dosage forms such as hard gelatin capsules comprising two types of beads—one bead population (IR beads) comprising sugar spheres drug layered from an aqueous solution of propranolol hydrochloride with polyvinylpyrrolidone as the binder and a second bead population (SR beads) comprising an immediate release bead population having a sustained release membrane of approximately 1.5 to 6%, more particularly 1.8 to 4.4% by weight of a water insoluble polymer alone or in combination with a water soluble film forming polymer, wherein the ratio of IR beads to SR beads as well as the ratio of water insoluble polymer to water soluble polymer is optimized to obtain release profiles similar to that of INDERAL® LA, when both reference product and the long acting capsules of the present invention are tested by the United States Pharmacopoeia method for Propranolol Hydrochloride Extended Release Capsules. It is another embodiment of the present invention to provide unit dosage forms to be bioequivalent to INDERAL® LA when compared on an mg-by-mg basis. It is yet another embodiment of the present invention to provide physically and chemically stable dosage forms (i.e., exhibiting drug release profiles and degradation profiles statistically similar to that at the initial time point) when subjected to stability studies per ICH Guidelines. These and other embodiments, advantages and features of the present invention become clear when detailed description and examples are provided in subsequent sections.

DETAILED DESCRIPTION OF THE INVENTION

Figure 1:
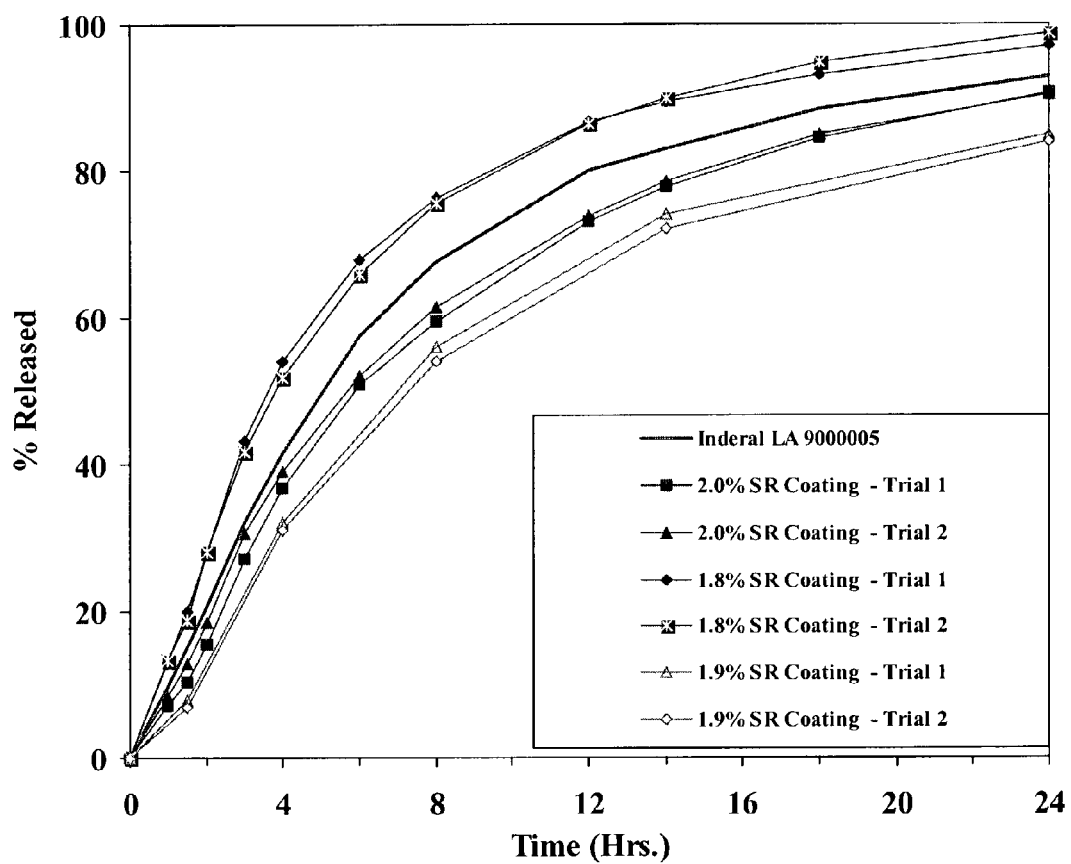
FIG. 1 illustrates non-reproducibility in drug release profiles for commercial scale batches of extended release propranolol HCl Capsules (duplicate bead batches coated with an ethylcellulose membrane at 2.0%, 1.9%, and 1.8% based on the weight of the coated beads as described in Example 1).

All documents cited are, in relevant part, incorporated herein by reference; the citation of any document is not to be construed as an admission that it is prior art with respect to the present invention.

As used herein, the term "propranolol" includes the base, pharmaceutically acceptable salts thereof, stereoisomers thereof and mixtures thereof.

The active core of the dosage form of the present invention may be comprised of an inert particle or an acidic or alkaline buffer crystal, which is coated with a drug-containing film-forming formulation and preferably a water-soluble film forming composition to form a water-soluble/dispersible particle. The amount of drug in the core will depend on the drug, the dose, and the capsule size. Those skilled in the art will be able to select an appropriate amount of drug for coating onto the core to achieve the desired dosage. In one embodiment, the inert core may be a sugar sphere, cellulose sphere, silicon dioxide or a buffer crystal or an encapsulated buffer crystal such as calcium carbonate, sodium bicarbonate, fumaric acid, tartaric acid, etc. which alters the microenvironment of the drug to facilitate its release.

The drug-containing particle may be coated with a water insoluble polymer or a combination of a water insoluble polymer and a water soluble polymer to provide SR beads. The water insoluble polymer and said water soluble polymer may be present at a weight ratio of from about 100/0 to 60/40 more particularly at a weight ratio of from about 95/5 to 65/35, preferably at a weight ratio of from 85/15 to 75/25. The membrane coating typically comprises from approximately 1% to 10%, preferably approximately 1.5 to 6%, most preferably approximately 1.8 to 4.4% by weight of the coated beads.

The unit dosage form according to one aspect of the present invention comprises two bead populations, one bead population, which provides an immediate release component of the active to act as a bolus dose and the other, a sustained release bead population, which releases propranolol over a period of 24 hours. In accordance with another embodiment, the dosage form comprises only SR beads.

The invention also provides a method of making a sustained release dosage form which comprises a mixture of two or more bead populations. In accordance with one aspect of the present invention, the method includes the steps of:
1. coating an inert particle such as a non-pareil seed, an acidic buffer crystal or an alkaline buffer crystal with a drug and polymeric binder to form an active drug particle (IR beads), which may be present in the unit dosage form to act as a bolus dose;
2. coating the active drug particle with a solution or suspension of a water insoluble polymer or a mixture of water soluble and water insoluble polymers to form a sustained release coated drug particle (SR beads);
3. filling into a hard gelatin capsule SR beads and IR beads at a proper ratio ranging from 95/5 to 70/30 (SR beads/ IR beads) to produce an extended release capsule exhibiting a drug release profile similar to that of INDERAL® LA when tested under identical conditions.

In accordance with certain embodiments of the present invention, the extended release capsule exhibits an in vitro dissolution profile substantially corresponding to the following pattern when tested according to United States Pharmacopoeia dissolution test method for Propranolol Hydrochloride Extended Release Capsules (USP Apparatus 1, Baskets @ 100 rpm, Drug Release Test 1 using 900 mL of pH 1.2 buffer for 1.5 hours followed by testing in 900 mL of pH 6.8 at 4, 8, 14, and 24 hours):

after 1.5 hours, not more than about 30% of the total propranolol is released;
after 4 hours, about 45±15%, preferably about 45±10%, of the total propranolol is released;

after 8 hours, about 65±15%, preferably about 65±10%, of the total propranolol is released;

after 14 hours, about 80±15%, preferably about 80±10%, of the total propranolol is released;

after 24 hours, not less than about 85% of the total propranolol is released.

An aqueous or a pharmaceutically acceptable solvent medium may be used for preparing drug containing core particles. The type of film forming binder that is used to bind the water-soluble drug to the inert sugar sphere is not critical but usually water-soluble, alcohol-soluble or acetone/water soluble binders are used. Binders such as polyvinylpyrrolidone (PVP), polyethylene oxide, hydroxypropyl methylcellulose (HPMC), hydroxypropylcellulose (HPC), and polysaccharides, such as dextran and cornstarch, typically are used at concentrations of 0.5 to 10 weight % based on the coating formulation. The drug substance may be present in this coating formulation in the solution form or may be suspended at a solid content up to 35 weight % or lower, depending on the viscosity of the coating formulation.

The active containing cores (beads, pellets or granular particles) thus obtained may be coated with one or more layers of polymers to obtain desired release profiles. The membrane coating, which largely controls the rate of drug release by diffusion following imbibition of water or body fluids into the core, comprises a water insoluble polymer or a water insoluble polymer in combination with a water-soluble polymer. The water insoluble polymer is selected from the group which includes ethylcellulose, cellulose acetate, and ammonio methacrylic acid copolymers sold under the trademarks EUDRAGIT RL and EUDRAGIT RS. The water-soluble polymer is selected from the group consisting of low viscosity (approximately 200 cps or less when tested as a 2% solution) HPMC, HPC, methylcellulose, polyethylene glycol (PEG of molecular weight>3000), and polyvinylpyrrolidone. The water insoluble polymer to water-soluble polymer ratio may typically vary 100/0 to 60/40, more particularly from 95/5 to 65/35, preferably from 85/15 to 75/25, at a thickness of from about 1% to 10%, preferably of approximately 1.5 to 6%, most preferably of approximately 1.8 to 4.4%, by weight of coated beads and depending on whether a polymer solution in an organic solvent or an aqueous polymer dispersion is used for membrane coating.

The membranes described herein may also include one or more plasticizers. Representative examples of plasticizers that may be used to plasticize the membranes include triacetin, tributyl citrate, triethyl citrate, acetyl tri-n-butyl citrate, diethyl phthalate, castor oil, dibutyl sebacate, acetylated monoglycerides and the like or mixtures thereof. The plasticizer may comprise about 3 to 30 wt. % and more typically about 10 to 25 wt. % based on the polymer.

In general, it is desirable to prime the surface of the active containing particle before applying the sustained release membrane coating by applying a thin hydroxypropyl methylcellulose (HPMC) film. A particularly useful plasticized HPMC seal coat is OPADRY® Clear available from Colorcon. While HPMC is typically used, other primer or seal coats such as hydroxypropyl cellulose (HPC) can also be used.

The present invention relates to multi-dose forms, i.e., drug products in the form of multi-particulate dosage forms (pellets, beads, granules or mini-tablets) or in other forms suitable for oral administration.

The following non-limiting examples illustrate the capsule dosage forms manufactured in accordance with the invention, which exhibit in vitro drug release profiles, similar to that predicted by performing modeling exercises, and in vitro and plasma concentrations following circadian rhythm pharmacodynamic profile of angina attacks.

Example 1

Propranolol HCl (168 kg) was slowly added to an aqueous solution of polyvinylpyrrolidone (8.8 kg Povidone K-30) and mixed well. 25-30 mesh sugar spheres (117.2 kg) were coated with the drug solution in a Glatt fluid bed granulator. The drug containing pellets were dried, and a seal coat of Opadry Clear (6.0 kg) was first applied. Duplicate batches of sustained release beads with a membrane coating with ethylcellulose having a viscosity of 10 cps at 25° C. at a thickness of 1.8%, 1.9% and 2.0% w/w (batch size: 275 kg) were manufactured. The SR coating was followed by the application of an Opadry Clear seal coating at 2% w/w. The SR beads prepared in accordance with Example 1 were filled into hard gelatin capsules and were characterized by the following properties:

Drug loading: 56% w/w based on core composition (corresponds to approximately 54% drug based on coated bead weight for bead batches having an SR coating of 1.8, 1.9, and 2.0%).

Drug Release Testing: The drug release profiles were generated by dissolution testing per US Pharmacopoeia method for Propranolol Hydrochloride Extended Release Capsules (USP Apparatus 1, Baskets @ 100 rpm, Drug Release Test 1 using 900 mL of pH 1.2 buffer for 1.5 hours followed by testing in 900 mL of pH 6.8 at 4, 8, 14, and 24 hours). The profiles obtained are shown in FIG. 1, which demonstrates potential batch to batch variability. Although ethylcellulose applied from a solvent solution provides less than ideal reproducibility, sustained release membranes containing ethylcellulose as described above are within the scope of the present invention.

Example 2

Figure 2:
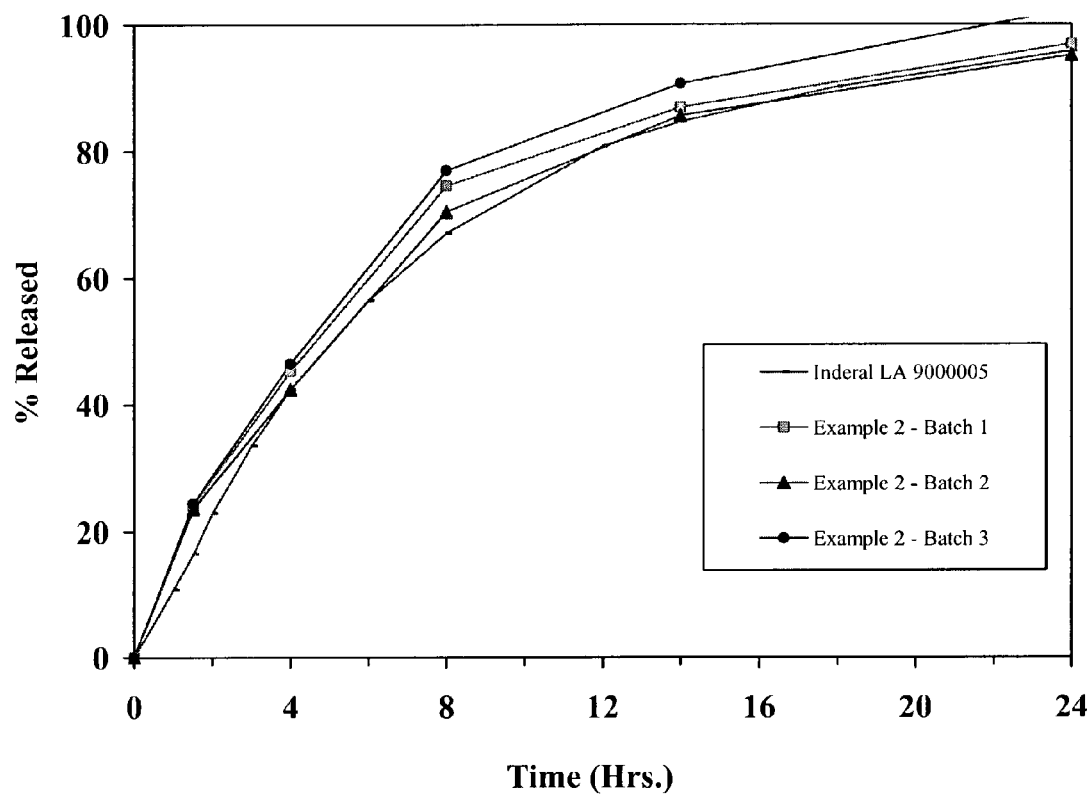
FIG. 2 shows drug release profiles for Extended Release Propranolol HCl Capsule, 160 mg (80% SR beads/20% IR beads) as described in Example 2.

Propranolol HCl (168 kg) was slowly added to an aqueous solution of polyvinylpyrrolidone (8.8 kg Povidone K-30) and mixed well. 25-30 mesh sugar spheres (117.2 kg) were coated with the drug solution in a Glatt fluid bed granulator. The drug containing pellets were dried, and a seal coat of Opadry Clear (6.0 kg) was first applied at a weight gain of 2% to form IR beads. Duplicate batches of sustained release beads were prepared by membrane coating IR beads (3750 g) with a sustained release coating comprising ethylcellulose (148 g) having a viscosity of 10 cps at 25° C. and hydroxypropylcellulose (Klucel LF; 47.3 g) having a viscosity of 75-150 cps when tested on a 5% aqueous solution at 25° C. (ratio of ethylcellulose to Klucel: 75/25) for a weight gain of approximately 5% w/w (batch size: 3947 g). The coated beads were cured at 60° C. for 4 hours. Propranolol Hydrochloride Extended Release Capsules, 160 mg, were produced by filling IR and SR Beads at a ratio of 20/80. The drug release from these capsules is presented in FIG. 2.

Example 3

Figure 3:
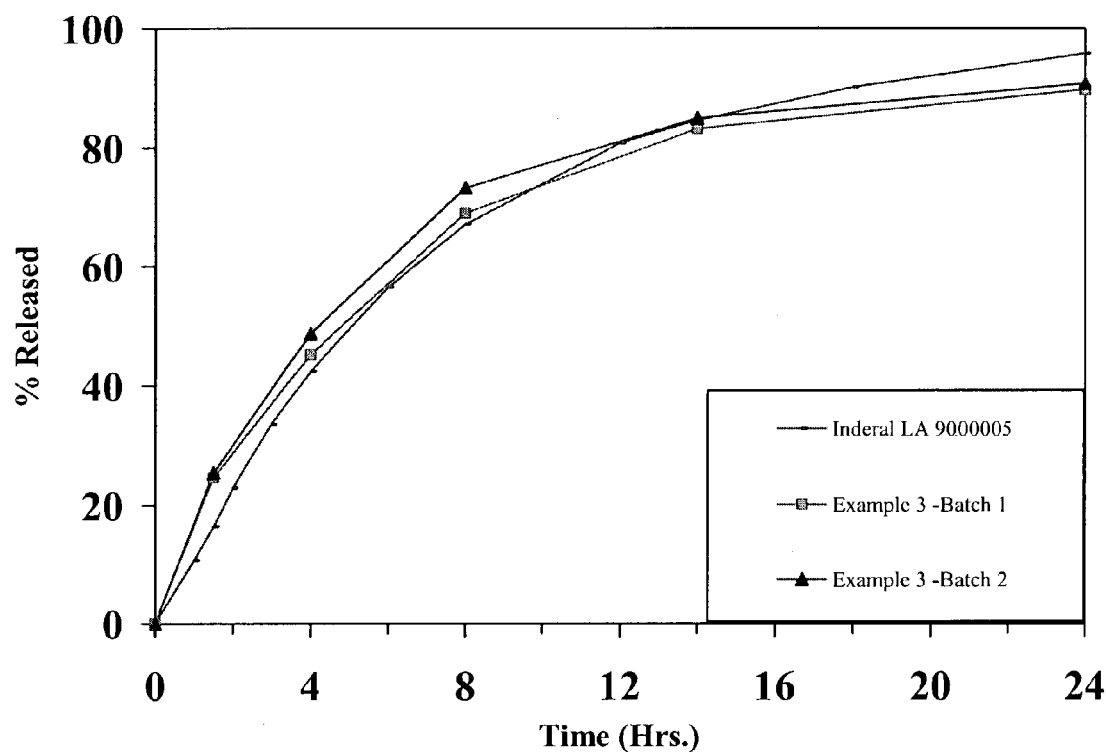
FIG. 3 illustrates drug release profiles for Extended Release Propranolol HCl Capsule, 160 mg (80% SR beads/ 20% IR beads) as described in Example 3.

Propranolol HCl (168 kg) was slowly added to an aqueous solution of polyvinylpyrrolidone (8.8 kg Povidone K-30) and mixed well. 25-30 mesh sugar spheres (117.2 kg) were coated with the drug solution in a Glatt fluid bed granulator. The drug containing pellets were dried, and a seal coat of Opadry Clear (6.0 kg) was first applied to form IR beads. Duplicate batches of sustained release beads were prepared by membrane coating IR beads (3750 g) with ethylcellulose (152.5 g) having a viscosity of 10 cps at 25° C. and hydroxypropyl methylcellulose (Methocel E5 from Dow Chemicals; 26.9 g) having a viscosity of 5 cps when tested on a 2% aqueous solution at 25° C. (ratio of ethylcellulose to Methocel E5: 85/15) for a weight gain of approximately 5% w/w (batch size: 3947 g). The coated beads were cured at 60° C. for 4 hours. Propranolol Hydrochloride Extended Release Capsules, 160 mg, were produced by filling IR and SR Beads at a ratio of 20/80. The drug release from these capsules is presented in FIG. 3.

Example 4

Figure 4:
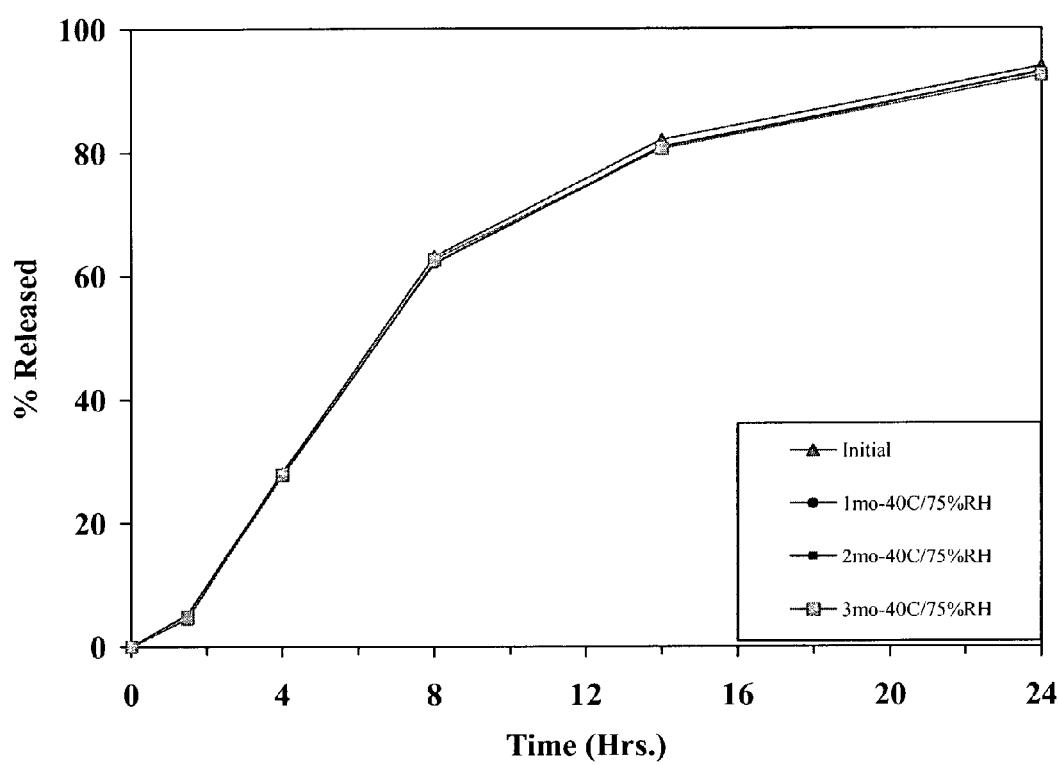
FIG. 4 provides drug release profiles for Extended Release Propranolol HCl Capsules on stability at 40° C./75% RH as described in Example 4.

Ethylcellulose-Klucel based extended release capsules of Example 2 were packaged in induction sealed HDPE bottles and placed on accelerated stability (i.e., at 40° C./75% RH). The drug release profiles at 1, 2, 3, and 6-month stability time points are shown in FIG. 4. These dissolution data as well as the chemical stability data demonstrate that the product is stable.

Example 5

Figure 5:
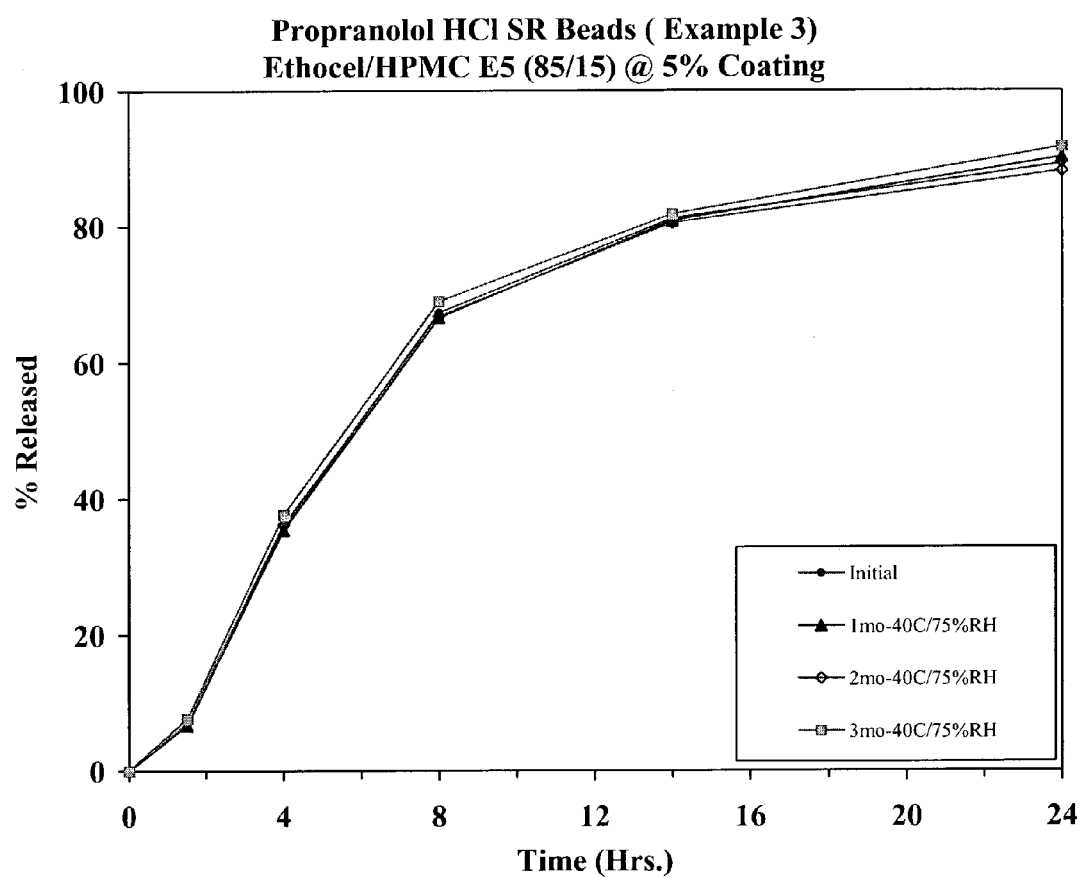
FIG. 5 shows drug release profiles for Extended Release Propranolol HCl Capsules on stability at 40° C./75% RH as described in Example 5.

Ethylcellulose-HPMC based extended release capsules of Example 3 were packaged in induction sealed HDPE bottles and placed on accelerated stability (i.e., at 40° C./75% RH). The drug release profiles at 1, 2, 3, and 6-month stability time points are shown in FIG. 5. These dissolution data as well as the chemical stability data demonstrate that the product is stable.

Example 6

Propranolol HCl (168 kg) was slowly added to an aqueous solution of polyvinylpyrrolidone (8.8 kg Povidone K-30) and mixed well. 25-30 mesh sugar spheres (117.2 kg) were coated with the drug solution in a Glatt fluid bed granulator. The drug containing pellets were dried, and a seal coat of OPADRY Clear (6.0 kg) was first applied to provide IR beads. IR beads (255.8 kg) were membrane coated with a sustained release coating comprising ethylcellulose (14.4 g) and hydroxypropyl methylcellulose (4.8 g) at a ratio of 75/25 for a weight gain of approximately 5% w/w (batch size: 275 kg). The coated beads were cured at 60° C. for 4 hours. Propranolol Hydrochloride Extended Release Capsules, 60, 80, 120, and 160 mg were produced by filling IR and SR Beads at a ratio of 20/80. The drug release from these capsules mimics that of INDERAL® LA.

What is claimed is:

1. A pharmaceutical dosage form comprising sustained release (SR) beads and optionally immediate release (IR) beads, wherein:
   a. said IR beads comprise core particles comprising propranolol or a pharmaceutically acceptable salt thereof, and mixtures thereof; and
   b. said SR beads comprise core particles comprising propranolol or a pharmaceutically acceptable salt thereof, and mixtures thereof; and a membrane comprising a water insoluble polymer or a combination of a water insoluble polymer and a water soluble polymer,
   wherein said pharmaceutical dosage form when tested according to United States Pharmacopoeia dissolution test method USP Apparatus 1, Baskets @ 100 rpm, Drug Release Test 1 using 900 mL of pH 1.2 buffer for 1.5 hours followed by testing in 900 mL of pH 6.8 at 4, 8, 14, and 24 hours, exhibits the following dissolution profile:
   after 1.5 hours, not more than about 30% of the total propranolol is released;
   after 4 hours, about 45±15% of the total propranolol is released;
   after 8 hours, about 65±15% of the total propranolol is released;
   after 14 hours, about 80±15% of the total propranolol is released; and
   after 24 hours, not less than about 85% of the total propranolol is released.

2. The pharmaceutical dosage form of claim 1 wherein said dissolution profile corresponds to the following pattern:
   after 1.5 hours, not more than about 30% of the total propranolol is released;
   after 4 hours, about 45±10% of the total propranolol is released;
   after 8 hours, about 65±10% of the total propranolol is released;
   after 14 hours, about 80±10% of the total propranolol is released; and
   after 24 hours, not less than about 85% of the total propranolol is released.

3. The pharmaceutical dosage form of claim 1, wherein the immediate release (IR) beads and Sustained Release (SR) beads are present in a ratio of IR beads to SR beads of from about 0:100 to 30:70.

4. The pharmaceutical dosage form of claim 1, comprising said IR beads, wherein said IR beads release substantially all of the propranolol contained therein during the first hour of dissolution testing.

5. The pharmaceutical dosage form of claim 1 wherein said water insoluble polymer is selected from the group consisting of ethylcellulose, cellulose acetate, ammonio methacrylic acid copolymers, and mixtures thereof.

6. The pharmaceutical dosage form of claim 1, wherein said coating comprises a water insoluble polymer in combination with a water soluble polymer.

7. The pharmaceutical dosage form of claim 1 wherein said core particles comprise sugar spheres, cellulose spheres, silicone dioxide spheroids, acidic buffer crystals, or alkaline buffer crystals.

8. The pharmaceutical dosage form of claim 1, wherein said core particles further comprise a polymeric binder.

9. The pharmaceutical dosage form of claim 1 wherein said core particles further comprise a seal coating.

10. The pharmaceutical dosage form of claim 1 wherein said water soluble polymer is selected from the group consisting of hydroxypropylcellulose, hydroxypropylmethylcellulose, methylcellulose, polyethylene glycol, and polyvinylpyrrolidone.

11. The pharmaceutical dosage form of claim 6 wherein said water insoluble polymer and water soluble polymer are present in a weight ratio of from about 0:100 to 60:40.

12. The pharmaceutical dosage form of claim 1 wherein the membrane comprises about 1% to 10% based on the weight of said SR beads.

13. The pharmaceutical dosage form of claim 5 wherein said water insoluble polymer comprises ethylcellulose having a viscosity of not more than 30 cps when tested on a 5% solution at 25° C.

14. The pharmaceutical dosage form of claim 1 wherein said dosage form contains a total of from about 60 mg to 160 mg propranolol or a pharmaceutically acceptable salt thereof.

15. The pharmaceutical dosage form of claim 6, wherein said water soluble polymer has a viscosity of not more than 200 cps when tested on a 2% aqueous solution at 25° C.

16. The pharmaceutical dosage form of claim 1, wherein said coating comprises approximately 1.5% to 6% based on the weight of the SR beads.

17. A method of providing a patient with a sustained release delivery of propranolol comprising administering to said patient the pharmaceutical dosage form of claim 1.

18. The method of claim 17 wherein said dosage form comprises a capsule.

19. The pharmaceutical dosage form of claim 7, wherein said core particles of said IR beads comprise nonpareil seeds and a polymeric binder.

20. A method of preparing a pharmaceutical dosage form, comprising the steps of:
 a. layering a solution comprising propranolol, a pharmaceutically acceptable salt thereof, or mixtures thereof, and a binder on inert particles to prepare immediate release (IR) beads;
 b. applying a sustained release coating, comprising a water insoluble polymer or a water insoluble polymer in combination with a water soluble polymer to the IR beads of step a, thereby forming sustained release (SR) beads; and
 c. filling capsules with SR beads of step b and optionally the IR beads of step a,
 wherein said filled capsules when tested according to United States Pharmacopoeia dissolution test method USP Apparatus 1, Baskets @ 100 rpm, Drug Release Test 1 using 900 mL of pH 1.2 buffer for 1.5 hours followed by testing in 900 mL of pH 6.8 at 4, 8, 14, and 24 hours, exhibit the following dissolution profile:
 after 1.5 hours, not more than about 30% of the total propranolol is released;
 after 4 hours, about 45±15% of the total propranolol is released;
 after 8 hours, about 65±15% of the total propranolol is released;
 after 14 hours, about 80±15% of the total propranolol is released; and
 after 24 hours, not less than about 85% of the total propranolol is released.

21. The method of claim 20, comprising the IR beads of step a, where said IR beads release substantially all of the propranolol contained therein within the first hour of dissolution testing.

22. The method of claim 20 wherein step (a) further comprises:
 applying a protective seal coat to the IR beads.

23. The method of claim 20, wherein said filled capsules comprise the IR beads of step a and the SR beads of step b at a ratio of from about 5:95 to 30:70 (IR beads:SR beads).

24. The method of claim 20, comprising the IR beads of step a, wherein the IR beads comprise beads, pellets, granules, or mini-tablets.

25. The method of claim 20, comprising the IR beads of step a, wherein the IR beads comprise sugar spheres, cellulose spheres, silicone dioxide spheroids, acidic buffer crystals, or alkaline buffer crystals, coated with propranolol and a polymeric binder.

* * * * *